United States Patent [19]

Morel

[11] 4,399,301
[45] Aug. 16, 1983

[54] METHYLENICALLY-SUBSTITUTED UNDECADIENES

[75] Inventor: Didier Morel, Lyon, France

[73] Assignee: Rhone-Poulenc Industries, Paris, France

[21] Appl. No.: 75,216

[22] Filed: Sep. 13, 1979

[30] Foreign Application Priority Data

Sep. 15, 1978 [FR] France ................... 78 26509

[51] Int. Cl.³ ............ C07C 33/02; C07C 43/15; C07C 43/215; C07C 69/007; C07C 69/145; C07C 69/24
[52] U.S. Cl. ...................... 560/261; 560/1; 560/113; 560/129; 560/201; 560/225; 560/244; 560/249; 568/631; 568/632; 568/657; 568/687; 568/690; 568/840; 568/875; 568/904
[58] Field of Search .............. 560/261, 244, 113, 129, 560/249, 201, 1, 225; 568/632, 904, 840, 657, 631, 687, 690

[56] References Cited

U.S. PATENT DOCUMENTS 3,728,260 3/1974 Hattori et al. ............... 560/261
3,981,907 9/1976 Hattori et al. ............... 560/261

OTHER PUBLICATIONS

Morita et al., Nippon Kagaku Zasshi, vol. 92, 1971, pp. 861–864.

*Primary Examiner*—Vivian Garner
*Attorney, Agent, or Firm*—Burns, Doane, Swecker & Mathis

[57] ABSTRACT

Methylenically-substituted undecadiene compounds having the structural formula:

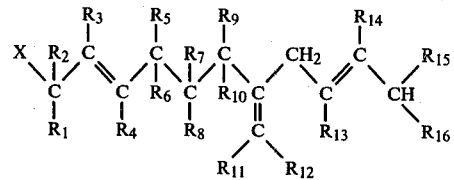

wherein X is selected from the group consisting of lower acyloxy, aryloxy having from 6 to 14 carbon atoms, lower alkoxy and hydroxy, and $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$, $R_{15}$ and $R_{16}$ are independently selected from the group consisting of hydrogen and lower alkyl, with the proviso that at least one of $R_3$, $R_5$ and $R_6$ and at least one of $R_9$, $R_{10}$, $R_{11}$ and $R_{12}$ must be hydrogen, are prepared by reacting a diene having the structural formula:

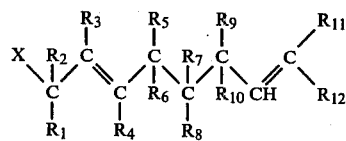

with a conjugated diene having the structural formula:

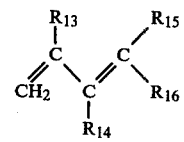

in the presence of a rhodium/trivalent phosphorus catalyst, with the atomic ratio of the trivalent phosphorus to the rhodium therein being at least 1.5. The compounds can be hydrogenated and saponified to form known alcohols which are precursors for biodegradable detergents.

10 Claims, No Drawings

METHYLENICALLY-SUBSTITUTED UNDECADIENES

BACKGROUND OF THE INVENTION

1. Field of the Invention

The present invention relates to novel methylenically-substituted undecadiene, and to a novel process for the preparation thereof. By "methylenically-substituted" as utilized herein, there are intended not only methylene, $=CH_2$, derivatives, per se, but also derivatives of the type, $=CHR$ and $=CRR$, wherein R is lower alkyl.

2. Description of the Prior Art

The addition of conjugated dienes to straight chain dimers of butadiene is a known reaction. French Pat. No. 2,077,072 discloses such an addition reaction and, in particular, features the reaction between a 1,3 conjugated diene having the structural formula:

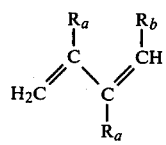

and a substituted butadiene dimer having the structural formula:

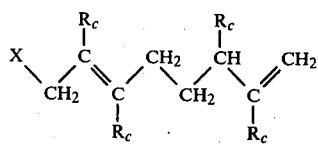

wherein $R_a$ and $R_c$ are selected from the group consisting of hydrogen and lower alkyl, $R_b$ is selected from the group consisting of hydrogen, lower alkyl and lower alkenyl, and X is selected from the group consisting of lower acyloxy, aryloxy having from 6 to 14 carbon atoms, lower alkoxy and hydroxy.

The aforementioned French patent discloses that the reaction produces two compounds, one having a straight chain structure wherein the carbon atom in the 8 position of the 1-substituted alkadiene is linked with the terminal carbon atom of the 1,3 conjugated diene, and the other having a structure wherein the 2-carbon atom of the 1-substituted alkadiene is linked with the terminal carbon atom of the 1,3 conjugated diene. An example given in the patent involves the reaction between 1,3 butadiene having the structural formula:

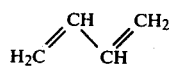

and 1-acetoxy-2,7-octadiene having the formula:

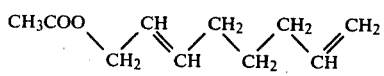

to prepare an 8-substituted derivative having the structural formula:

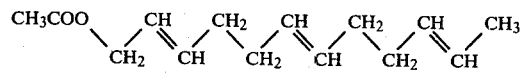

and its 2-substituted isomers having the structural formulas:

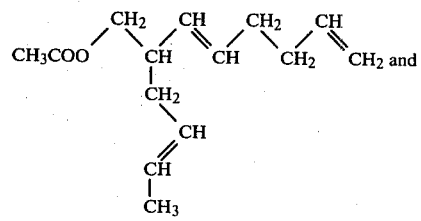

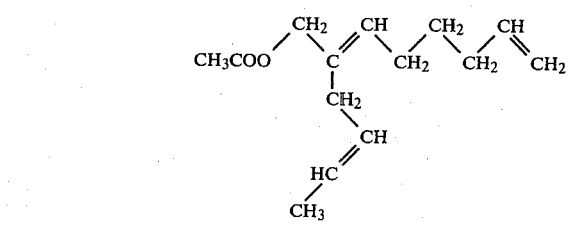

The French patent also discloses that the production of the 8-substituted derivative is favored when the addition takes place in the presence of a trivalent phosphorus compound such as triphenylphosphine, tri-n-butylphosphine, tri-isopropylphosphine, tricyclohexylphosphine, phenyldichlorophosphine, phosphorus trichloride and triphenylphosphate. According to the examples given in the French patent, the atomic ratio of the trivalent phosphorus to rhodium present is less than or equal to 1.

SUMMARY OF THE INVENTION

It has now surprisingly been found, and which is a major object of the invention, that the reaction between 1,3 butadiene and 1-acetoxy-2,7-octadiene in the presence of a rhodium/trivalent phosphorus catalyst wherein the atomic ratio of the trivalent phosphorus to the rhodium is at least 1.5 yields as the principal product the methylenically-substituted undecadiene having the structural formula:

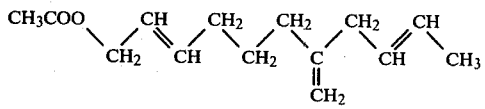

The appearance of said methylenically-substituted undecadiene, even as a secondary compound, is not disclosed in the prior art. Although the above methylenically-substituted undecadiene is the product obtained in the highest yield, it should be understood that 8-substituted and 2-substituted isomers are obtained as secondary products.

More generally, it has been surprisingly found that conjugated dienes and substituted dimers of alkadienes react to form methylenically-substituted undecadienes in the presence of a rhodium/trivalent phosphorus catalyst wherein the atomic ratio of the trivalent phosphorus to the rhodium therein is at least 1.5.

DETAILED DESCRIPTION OF THE INVENTION

One object of this invention is to provide a methylenically-substituted undecadiene having the structural formula:

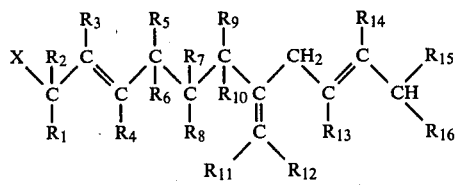  (I)

wherein X is selected form the group consisting of lower acyloxy, aryloxy having from 6 to 14 carbon atoms, lower alkoxy and hydroxy, and $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$, $R_{15}$ and $R_{16}$ are independently selected from the group consisting of hydrogen and lower alkyl, which preferably contains from 1 to about 3 carbon atoms, with the proviso that at least one of $R_3$, $R_5$ and $R_6$ and at least one of $R_9$, $R_{10}$, $R_{11}$ and $R_{12}$ must be hydrogen.

In a preferred embodiment of this invention, the methylenically-substituted undecadiene compounds of the present invention comprise compounds such as those defined hereinabove wherein $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$, $R_{15}$ and $R_{16}$ are independently selected from the group consisting of hydrogen and methyl, with the proviso that at least one of $R_3$, $R_5$ and $R_6$ and at least one of $R_9$, $R_{10}$, $R_{11}$ and $R_{12}$ are hydrogen.

In a more specific embodiment, the compounds of this invention are those of Formula (I) wherein all of the R-s are hydrogen. For example, a preferred compound of the present invention is 1-acetoxy-7-methylene-2,9-undecadiene which has the structural formula:

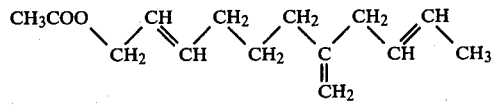

Another object of this invention is to provide a process for the preparation of the compounds of Formula (I). The process comprises the reaction of a diene having the structural formula:

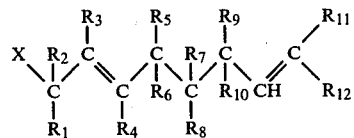  (II)

with a conjugated diene having the structural formula:

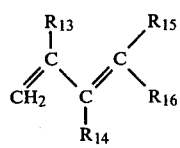  (III)

wherein X is selected from the group consisting of lower acyloxy, aryloxy having from 6 to 14 carbon atoms, lower alkoxy and hydroxy, and $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$, $R_{15}$ and $R_{16}$ are independently selected from the group consisting of hydrogen and lower alkyl, which preferably contains from 1 to about 3 carbon atoms, with the proviso that at least one of $R_3$, $R_5$ and $R_6$ and at least one of $R_9$, $R_{10}$, $R_{11}$ and $R_{12}$ are hydrogen, in the presence of a rhodium/trivalent phosphorus catalyst, with the atomic ratio of the trivalent phosphorus to the rhodium therein being at least 1.5.

The atomic ratio of trivalent phosphorus to rhodium in the catalyst of the present invention is at least 1.5, preferably in the range of about 1.5 to about 10 and more preferably in the range of about 2 to about 6. Rhodium is preferably employed in the form of the inorganic acid salts of rhodium, such as, for example, $RhCl_3$. The trivalent phosphorus can be employed in the form of a trivalent phosphorus compound which is preferably selected from the group consisting of the aryl and alkyl phosphines, for example, triphenylphosphine and bis-1,2-(diphenylphosphino)-ethylene which has the structural formula:

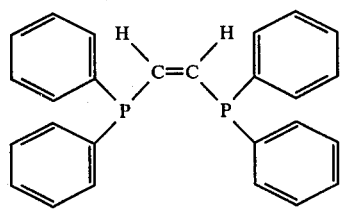

A specific example of a suitable catalyst for the process of this invention, therefore, is a catalyst comprising triphenylphosphine and $RhCl_3$ wherein the atomic ratio of trivalent phosphorus to rhodium therein is at least 1.5.

The present invention is particularly applicable to a process such as the one defined hereinabove wherein a compound of Formula (II) and a compound of Formula (III) are employed in which $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$, $R_{15}$ and $R_{16}$ are independently selected from the group consisting of hydrogen and methyl with the proviso that at least one of $R_3$, $R_5$ and $R_6$ and at least one of $R_9$, $R_{10}$, $R_{11}$ and $R_{12}$ must be hydrogen. Exemplifying such a process is the reaction of 1-acetoxy-2,7-octadiene having the structural formula:

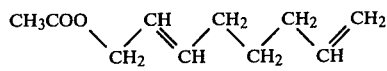

with 1,3-butadiene having the structural formula:

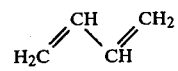

to obtain 1-acetoxy-7-methylene-2,9-undecadiene.

Additional examples of reactions according to the invention are of 2,7-octadiene-1-ol with 1,3-butadiene to yield 7-methylene-2,9-undecadiene-1-ol and the reaction of 1-methoxy-2,7-octadiene with 1,3-butadiene to yield 1-methoxy-7-methylene-2,9-undecadiene. Additional examples of suitable compounds of Formula (II) are 1-acetoxy-2,6-dimethyl-2,7-octadiene, 1-methoxy-2,6-dimethyl-2,7-octadiene, 2-acetoxy-3,8-decadiene, 2-methoxy-3,8-decadiene and 3,8-decadiene-2-ol. Additional examples of suitable compounds of Formula (III) are isoprene and piperylene.

The process of the present invention can be operated under a wide range of operating parameters, but, generally, is operated in the range of about 90° to about 150° C.

The general mode of operation can be exemplified as follows: a stainless steel autoclave is used and the reagents are introduced under an inert atmosphere, preferably in the following order; rhodium, trivalent phosphorus, ethanol, substituted conjugated diene dimer and the conjugated diene. The ethanol, which is used in small amounts, serves to activate the catalyst and is therefor preferably employed.

The mixture is heated under agitation. When the reaction is terminated, the residual conjugated diene is eliminated by degassing. The product of the reaction is then isolated from the mixture obtained by distillation under reduced pressure.

The product obtained, which corresponds to Formula (I), can be used after hydrogenation and saponification as an intermediate compound for the preparation of well-known alcohols which are precursors for art recognized and well-known compounds known for their usefulness as biodegradable detergents.

The substituted dienes of Formula (II) can be prepared by methods found in the prior art. In particular, they can be prepared by reacting conjugated dienes with compounds containing active hydrogen in the presence of palladium catalysts.

The invention will be described more completely with the aid of the following examples which are not meant to be limiting to the invention in any way, but are merely meant to be illustrative.

EXAMPLE 1

1-acetoxy-7-methylene-2,9-undecadiene was prepared from 1,3-butadiene and 1-acetoxy-2,7-octadiene by employing a catalyst having an atomic ratio of trivalent phosphorus/rhodium of about 3.

Into a stainless steel 125 cm$^3$ autoclave were introduced 0.112 g RhCl$_3$.4H$_2$O (0.4 millimole), 0.314 g triphenylphosphine (1.2 millimole), 2.60 g ethanol, 20 g 1-acetoxy-2,7-octadiene and 11 g butadiene. The mixture was heated under agitation at 120° C. for 6½ hours. The unreacted butadiene is eliminated and 32.4 g of a red, homogeneous reaction mixture were obtained; gaseous phase chromatography, NMR and mass spectrography analyses confirmed that the mixture comprised 0.82 g of branched chain compound having the structural formula:

$$CH_3COO-CH_2-C(=CH_2)-CH_2-CH_2-CH_2-CH=CH_2$$
$$\quad\quad\quad\quad\quad\quad\quad\quad CH_2-CH=CH-CH_3$$

1.12 g of a linear compound of the structural formula:

$$CH_3COO-CH_2-CH=CH-CH_2-CH_2-CH=CH-CH_2-CH=CH-CH_3$$

and 10.06 g of the methylenically-substituted undecadiene having the structural formula (boiling point 80°–84° C. under 0.2 mm Hg)

$$CH_3COO-CH_2-CH=CH-CH_2-CH_2-C(=CH_2)-CH=CH-CH_3$$

together with 5 g of unreacted 1-acetoxy-2,7-octadiene, 2.2 g of alcohol obtained via transesterification between the acetoxy and ethanol, with the remainder consisting principally of oligomers of butadiene. The conversion of the 1-acetoxy-2,7-octadiene was 75%. The selectivity of 1-acetoxy-7-methylene-2,7-undecadiene was 84%.

EXAMPLE 2

1-acetoxy-7-methylene-2,9-undecadiene was prepared from 1,3-butadiene and 1-acetoxy-2,7-octadiene. The catalyst employed had an atomic ratio of trivalent phosphorus to rhodium of about 2.

The mode of operation was as in Example 1 except that 0.210 g of triphenylphosphine (0.8 millimole) was used. The following products were obtained:
0.72 g of branched chain compound,
2.10 g of linear compound, and
7.67 g of the invention compound (1-acetoxy-7-methylene-2,9-undecadiene).

The selectivity with respect to the inventive product was 73% with a transformation rate of the 1-acetoxy-2,7-octadiene of 79%.

EXAMPLE 3

(Comparative example)

1-acetoxy-7-methylene-2,9-undecadiene was prepared from 1,3-butadiene and 1-acetoxy-2,7-octadiene. A catalyst was employed wherein the atomic ratio of trivalent phosphorus to rhodium was about 1.

The operation was effected under the same conditions as in Example 1 except that only 0.105 g of triphenylphosphine (0.4 millimole) was used.

33.1 g of the reaction mixture were obtained, said mixture comprised:
3.06 g of branched chain compound,
6.6 g of linear compound, and
1.6 g 1-acetoxy-7-methylene-2,9-undecadiene.
The selectivity to 1-acetoxy-7-methylene-2,9-undecadiene was 15% and the conversion of the 1-acetoxy-2,7-octadiene was 77%.

This example clearly shows the effect of the ratio of the trivalent phosphorus to rhodium on the formation of the invention methylenically-substituted undecadiene compound.

EXAMPLE 4

1-acetoxy-7-methylene-2,9-undecadiene was prepared from 1,3-butadiene and 1-acetoxy-2,7-octadiene. A catalyst was employed wherein the atomic ratio of the trivalent phosphorus to rhodium was 3.

The operation was effected as in Example 1 except that the following were used: 0.056 g RhCl$_3$.4H$_2$O (0.2 millimole), 0.157 g triphenylphosphine (0.6 millimole) and 1 g ethanol.

The following products were obtained:
0.3 g of branched chain compound,
1.2 g of linear compound, and
9.8 g 1-acetoxy-7-methylene-2,7-undecadiene.

Selectivity to 1-acetoxy-7-methylene-2,7-undecadiene was 86%.

The rate of the transformation of 1-acetoxy-2,7-octadiene was 64%.

Because the quantity of the $RhCl_3.4H_2O$ used in this sample was lower, much less of the heavy products was obtained, with a rate of transformation that was not reduced in the same proportion as the amount of rhodium.

EXAMPLE 5

7-methylene-2,9-undecadiene-1-ol was prepared from 2,7-octadiene-1-ol and butadiene by employing a catalyst which had an atomic ratio of trivalent phosphorus to rhodium of 3.

Into a 125 cm³ stainless steel autoclave, 0.168 g $RhCl_3.4H_2O$ (0.6 millimole), 0.476 g triphenylphosphine (1.8 millimole), 0.8 g ethanol, 22.7 g 2,7-octadiene-1-ol and 9.8 g 1,3-butadiene were introduced. The mixture was heated under agitation at 120° C. for 6 hours. The unreacted butadiene was removed. 29.7 g of an orange liquid comprising some insoluble particles were obtained. Gaseous phase chromatography, IR, NMR and mass spectrography analyses confirmed that the reaction mixture obtained comprised:

2.7 g of the branched chain product having the structural formula:

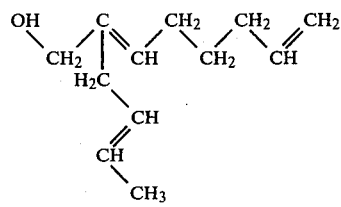

0.87 g of the linear product of the structural formula:

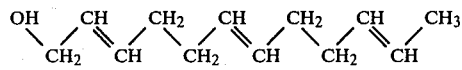

7 g 7-methylene-2,9-undecadiene-1-ol having the structural formula:

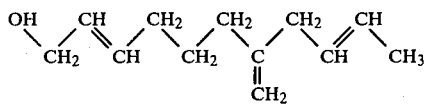

Selectivity to 7-methylene-2,9-undecadiene-1-ol was 67% with a transformation rate for 2,7-octadiene-1-ol of 77%.

EXAMPLE 6

1-acetoxy-7-methylene-2,9-undecadiene was prepared from 1,3-butadiene and 1-acetoxy-2,7-octadiene. The atomic ratio of trivalent phosphorus to rhodium employed in the catalyst was 4.

The operation was effected as in Example 4, except that 0.210 g of triphenylphosphine (0.8 millimole) and 0.8 g of ethanol were employed.

The following products were obtained:
0.11 g of branched chain compound,
0.8 g of linear compound, and
4.72 g 1-acetoxy-7-methylene-2,9-undecadiene.

Selectivity to 1-acetoxy-7-methylene-2,9-undecadiene was 84% with a rate of transformation of the 1-acetoxy-2,7-octadiene of 38%.

EXAMPLE 7

1-acetoxy-7-methylene-2,9-undecadiene was prepared from 1,3-butadiene and 1-acetoxy-2,7-octadiene by employing an atomic ratio of trivalent phosphorus to rhodium in the catalyst of 6.

The operation was effected as in Example 4, except that 0.314 g of triphenylphosphine (1.2 millimole) and 0.8 g ethanol were used.

The following products were obtained:
0.02 g of branched chain compound,
0.30 g of linear compound, and
2.23 g 1-acetoxy-7-methylene-2,9-undecadiene.

Selectivity in 1-acetoxy-7-methylene-2,9-undecadiene was 87% with a rate of transformation of 1-acetoxy-2,7-octadiene of 18%.

It should be noted that an atomic ratio of trivalent phosphorus to rhodium in excess of 3 did not increase the selectivity of the transformation of 1-acetoxy-7-methylene-2,9-undecadiene and did not reduce the rate of transformation of 1-acetoxy-2,7-octadiene.

EXAMPLE 8

1-methoxy-7-methylene-2,9-undecadiene was prepared from 1-methoxy-2,7-octadiene and 1,3-butadiene. The atomic ratio of trivalent phosphorus to rhodium in the catalyst was 3.

Into a 125 cm³ stainless steel autoclave, 0.056 g $RhCl_3.4H_2O$ (0.2 millimole), 0.157 g triphenylphosphine (0.6 millimole), 0.8 ethanol, 20 g 1-methoxy-2,7-octadiene and 8.8 g 1,3-butadiene were introduced. Under agitation, the mixture was heated at 120° C. for 6½ hours. The unreacted butadiene was eliminated and 29.2 g of an orange liquid were obtained.

Gaseous phase chromatography, infra red, NMR and mass spectrography analyses confirmed that the reaction mixture obtained comprised:
1.1 g of branched chain product,
1.5 g of linear product, and
11.37 g of 1-methoxy-7-methylene-2,9-undecadiene.

Selectivity to 1-methoxy-7-methylene-2,9-undecadiene was 82% with a rate of transformation of the 1-methoxy-2,7-octadiene of 90%.

EXAMPLE 9

1-methoxy-7-methylene-2,9-undecadiene was prepared from 1-methoxy-2,7-octadiene and 1,3-butadiene. The atomic ratio of trivalent phosphorus to rhodium was 5.

The operation was conducted as in Example 8 except that 0.262 g triphenylphosphine (1 millimole) were employed.

The following products were obtained:
0.21 g of branched chain compound,
0.9 g of linear compound, and
5.41 g 1-methoxy-7-methylene-2,9-undecadiene.

Selectivity to 1-methoxy-7-methylene-2,9-undecadiene was 83% with a rate of transformation of the 1-methoxy-2,7-octadiene of 40%.

Reasonable variations and modifications which will become apparent to those skilled in the art can be made in the present invention without departing from the spirit and scope thereof.

What is claimed is:

1. A methylenically-substituted undecadiene compound having the structural formula:

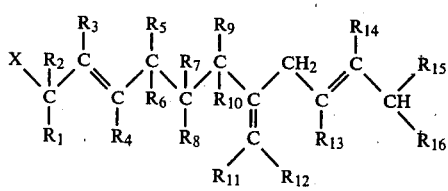

wherein X is selected from the group consisting of lower acyloxy, aryloxy having from 6 to 14 carbon atoms, lower alkoxy and hydroxy, and $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$, $R_{15}$ and $R_{16}$ are independently selected from the group consisting of hydrogen and lower alkyl, with the proviso that at least one of $R_3$, $R_5$ and $R_6$ and at least one of $R_9$, $R_{10}$, $R_{11}$ and $R_{12}$ must be hydrogen.

2. The compound of claim 1 wherein the lower alkyl contains from 1 to about 3 carbon atoms.

3. The compound of claim 1 wherein $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$, $R_{15}$ and $R_{16}$ are independently selected from the group consisting of hydrogen and methyl.

4. The compound of claim 1 wherein $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$, $R_{15}$ and $R_{16}$ are hydrogen.

5. The compound of claim 1 wherein X is an acyloxy.

6. The compound of claim 5 wherein X is acetoxy.

7. The compound of claim 1 wherein X is an aryloxy.

8. The compound of claim 1 wherein X is an alkoxy.

9. The compound of claim 8 wherein X is methoxy.

10. The compound of claim 1 which has the structural formula:

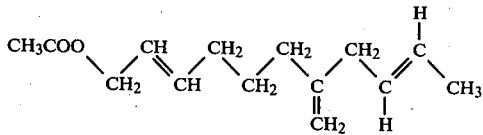

* * * * *